United States Patent [19]

Kato et al.

[11] Patent Number: 4,938,194
[45] Date of Patent: Jul. 3, 1990

[54] METHOD OF DETERMINING DETERIORATION OF OXYGEN CONCENTRATION SENSOR

[75] Inventors: Akira Kato; Toru Yano, both of Wako, Japan

[73] Assignee: Honda Giken Kogyo K. K., Tokyo, Japan

[21] Appl. No.: 372,297

[22] Filed: Jun. 27, 1989

[30] Foreign Application Priority Data

Jun. 30, 1988 [JP] Japan ............................. 63-162857

[51] Int. Cl.$^5$ ..................... F02D 41/14; F02D 41/22
[52] U.S. Cl. .................................. 123/479; 123/489
[58] Field of Search ............... 123/479, 440, 489; 204/401, 406

[56] References Cited

U.S. PATENT DOCUMENTS 4,819,602 4/1989 Mieno et al. ..................... 123/479
4,886,028 12/1989 Uchinami et al. ................. 123/479

FOREIGN PATENT DOCUMENTS

218058 10/1985 Japan .

*Primary Examiner*—Tony M. Argenbright
*Attorney, Agent, or Firm*—Arthur L. Lessler

[57] ABSTRACT

A method of determining the deterioration of an oxygen concentration sensor for an internal combustion engine. The oxygen concentration sensor includes at least one oxygen concentration sensor element having an oxygen-pumping element and a cell element each composed of a member of a solid electrolytic material having oxygen ion-conductivity, and a pair of electrodes having the member interposed therebetween, and a current-detecting resistance serially connected to the oxygen-pumping element to form a series circuit. A voltage having a magnitude corresponding to a difference between a voltage produced between the electrodes of the cell element and a predetermined reference voltage is applied to the series circuit, and pumping current is detected from a voltage developed across the current-detecting resistance. The predetermined reference voltage is changed from a first predetermined value to a second predetermined value, followed by detecting a difference between a value of said pumping current detected when the predetermined reference voltage assumes the first predetermined value and a value of the pumping current detected when the predetermined reference voltage assumes the second predetermined value. It is determined that there is deterioration in the oxygen concentration sensor when the difference is equal to or greater than a predetermined reference value.

14 Claims, 9 Drawing Sheets

METHOD OF DETERMINING DETERIORATION OF OXYGEN CONCENTRATION SENSOR

BACKGROUND OF THE INVENTION

This invention relates to a method of determining deterioration of an oxygen concentration sensor for sensing the concentration of oxygen in exhaust gases emitted from an internal combustion engine, and more particularly to a method of this kind, which utilizes an oxygen concentration sensor having an output characteristic such that the output thereof is proportional to the concentration of oxygen in the exhaust gases.

Electronic fuel supply control for internal combustion engines generally includes air-fuel ratio feedback control wherein the concentration of oxygen contained in exhaust gases emitted from the engine is detected, and the air-fuel ratio of a mixture actually supplied to the engine (hereinafter called "the actual air-fuel ratio") is controlled to a desired air-fuel ratio in a feedback manner responsive to the detected concentration value, in order to improve emission characteristics, fuel consumption, and so on. Conventional air-fuel ratio feedback control methods include methods using a proportional output type sensor as the oxygen concentration sensor, which has such an output characteristic as to produce an output proportional to the concentration of oxygen in the exhaust gases.

However, such proportional output type sensor is required to have an output accurately corresponding to the oxygen concentration for properly controlling the air-fuel ratio. However, after a long-term use, the sensor is apt to deteriorate mainly due to deposition of oxides in the exhaust gases on electrodes of an oxygen concentration sensor element of the sensor, failing to maintain a desired output characteristic.

Figure 8:
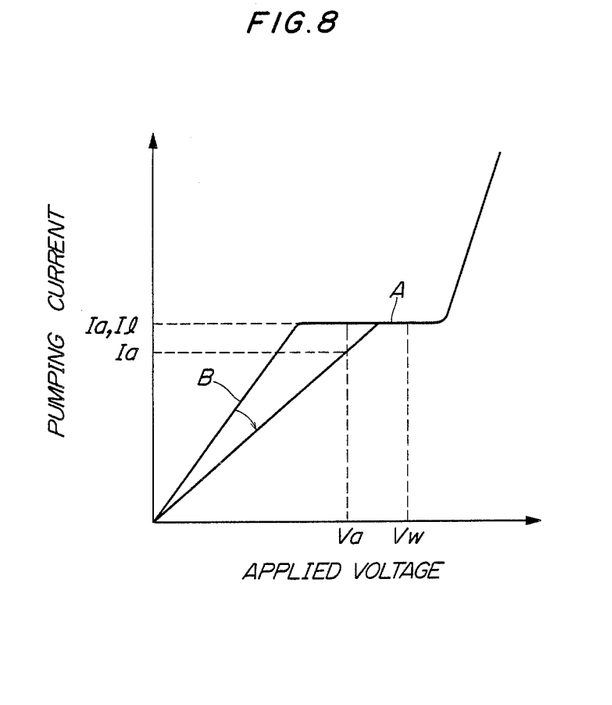
FIG. 8 is a graph showing the characteristic of pumping current relative to applied voltage.

To cope with the above problem, a method of determining deterioration of an oxygen concentration sensor has been proposed, e.g. by Japanese Provisional Patent Publication (Kokai) No. 60-218058 which utilizes the characteristic of output current (hereinafter referred to as "pumping current") produced from an oxygen concentration sensor element of the aforesaid type of oxygen concentration sensor that, as shown in FIG. 8, in which the pumping current is plotted with respect to voltage applied to the sensor element, the pumping current has a flat curve portion A where it assumes a constant value even when the applied voltage varies, and the inclination of a rising curve portion B decreases to shorten the flat curveportion A as the sensor element deteriorates. According to the proposed method, the determioration of the oxygen concentration sensor is determined by comparing between values Il and Ia of the pumping current respectively produced when two different voltages Vw and Va are applied to the sensor element.

However, in the above proposed method, the sensor element to which voltage is applied is the same element that has its pumping current detected. Therefore, when the pumping current flows through the sensor element, there arises a voltage drop porportional to the value of the pumping current across the sensor element due to the internal resistance thereof, so that the applied voltage is detected as the sum of the actual applied voltage and the voltage drop. Therefore, the deterioration of the sensor is judged based on the relationship between the inaccurately detected applied voltage and the pumping current value, which makes it impossible to determine the deterioration of the oxygen concentration sensor with accuracy.

SUMMARY OF THE INVENTION

It is the object of the invention to provide a method of determining deterioration of an oxygen concentration sensor, which is capable of determining deterioration of the sensor with imporoved accuracy.

To attain the above object, the present invention provides a method of determining the deterioration of an oxygen concentration sensor for an internal combustion engine, the oxygen concentration sensor including:
   at least one oxygen concentration sensor element, the oxygen concentration sensor element having an oxygen-pumping element and a cell element, the oxygen-pumping element and the cell element each being composed of a member of a solid electrolytic material having oxygen ion-conductivity, and a pair of electrodes having the member interposed therebetween, the oxygen-pumping element and the cell element defining a diffusion restriction region therebetween;
   a current-detecting resistance serially connected to the oxygen-pumping element to form a series circuit therewith;
   voltage-applying means for applying to the series circuit a voltage having a magnitude corresponding to a difference between a voltage produced between the electrodes of the cell element and a predetermined reference voltage; and
   current-detecting means for detecting pumping current from a voltage developed across the current-detecting resistance;
   the method comprising the steps of:
      (1) changing the predetermined reference voltage from a first predetermined value to a second predetermined value;
      (2) detecting a difference between a value of the pumping current detected when the predetermined reference voltage assumes the first predetermined value and a value of the pumping current detected when the predetermined reference voltage assumes the second predetermined value;
      (3) comparing the difference detected in the step (2) with a predetermined reference value; and
      (4) determining that there is deterioration in the oxygen concentration sensor when the difference is equal to or greater than the predetermined reference value.

Preferably, the oxygen concentration sensor includes first and second oxygen concentration sensor elements, and the steps (2)–(4) comprise:
   (2a) detecting a first difference between a value of the pumping current detected by the use of the first oxygen concentration sensor element when the predetermined reference voltage assumes the first predetermined value and a value of the pumping current detected by the use of the first oxygen concentraion sensor element when the predetermined reference voltage assumes the second predetermined value;
   (2b) detecting a second difference between a value of the pumping current detected by the use of the second oxygen concentration sensor element when the predetermined reference voltage assumes the first predetermined value and a value of the pumping current detected by the use of the second oxygen concentration sensor element when the predetermined reference voltage assumes the second predetermined value;

(3a) comparing the first difference with a first predetermined reference value;

(3b) comparing the second diffrence with a second predetermined reference value; and (4') determining that there is deterioration in the oxygen concentration sensor either when the first difference is equal to or greater than the first predetermined reference value or when the second difference is equal to or greater than the second predetermined reference value.

Further preferably, the step (2) comprises detecting a difference between a cumulated value of values of the pumping current detected a predetermined number of times when the predetermined reference voltage assumes the first predetermined value and a cumulated value of values of the pumping current detected the predetermined number of times when the predetermined reference voltage assumes the second predetermined value.

Still more preferably, the determination of deterioration of the oxygen concentration sensor is carried out when the engine is in a predetermined stable operating condition.

The above and other objects, features, and advantages of the invention will be more apparent from the ensuing detailed description taken in conjunction with the accompanying drawings.

DETAILED DESCRIPTION

The invention will now be described in detail with reference to the drawings showing an embodiment thereof.

Figures 1, 1A:
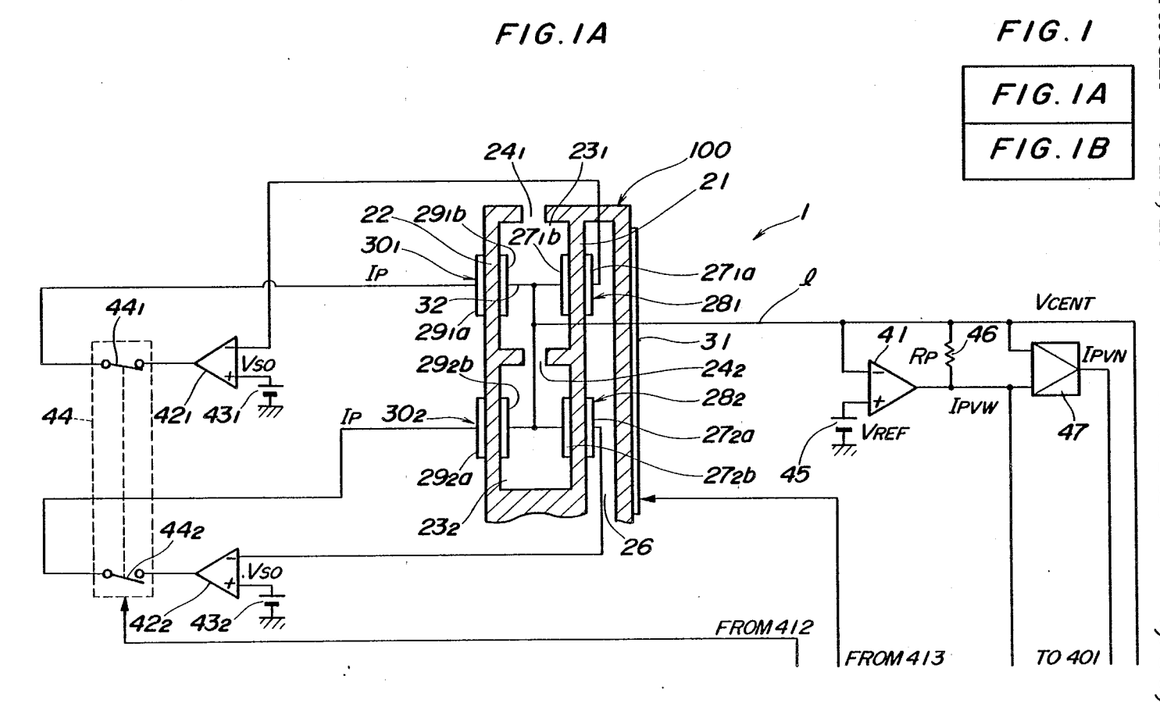
FIGS. 1, 1A and 1B are a schematic diagram of the overall arrangement of a fuel supply control system for an internal combustion engine equipped with an oxygen concentration ($O_2$) sensor to which the method of the invention is applied.
Figure 1B:
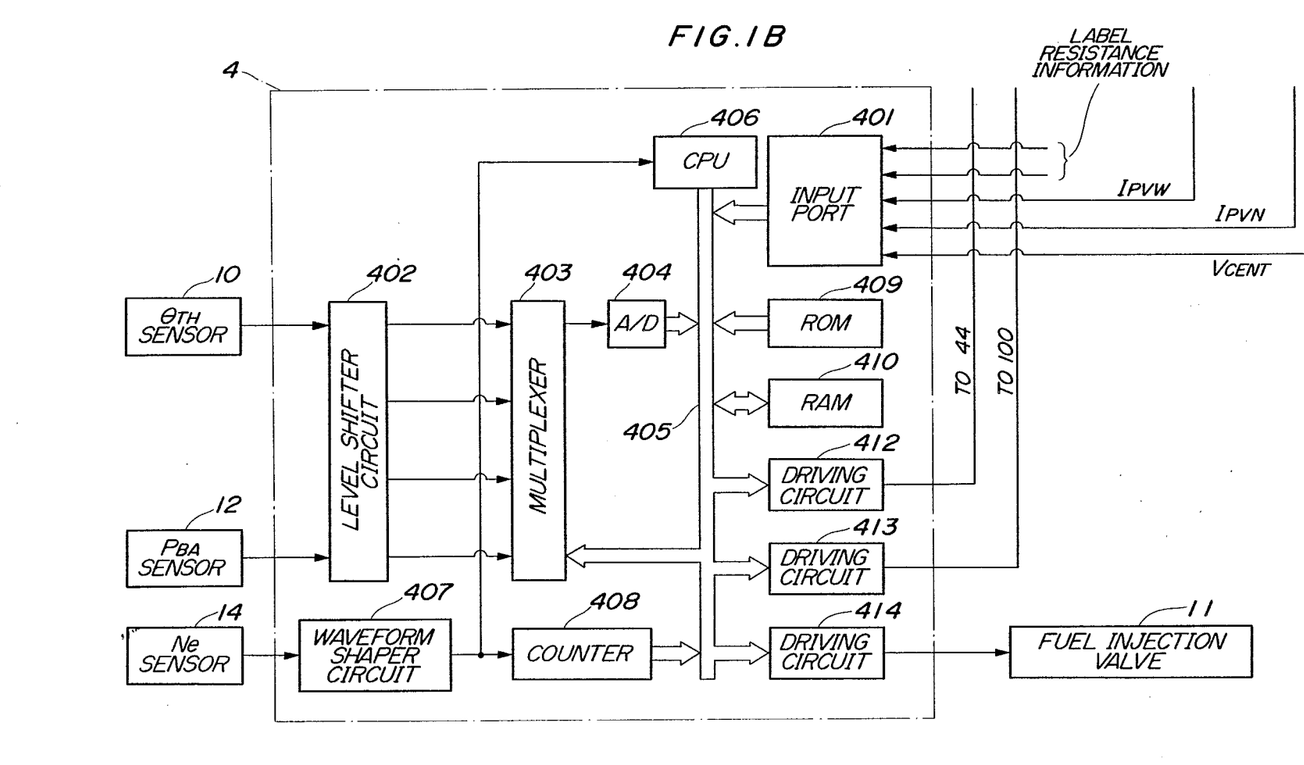

Referring first to FIG. 1, there is illustrated the whole arrangement of a fuel supply control system for an internal combustion engine including an oxygen concentration sensor to which the method according to the invention is applied.

In the figure, reference numeral 100 designates a body (sensor element section) of the oxygen concentration sensor (hereinafter called "the $O_2$ sensor) 1. The sensor body 100 is arranged within an exhaust system of an engine, not shown, in which a three-way catalyst is arranged for purifying ingredients HC, CO, and NOx contained in the exhaust gases emitted from the engine.

Figure 2:
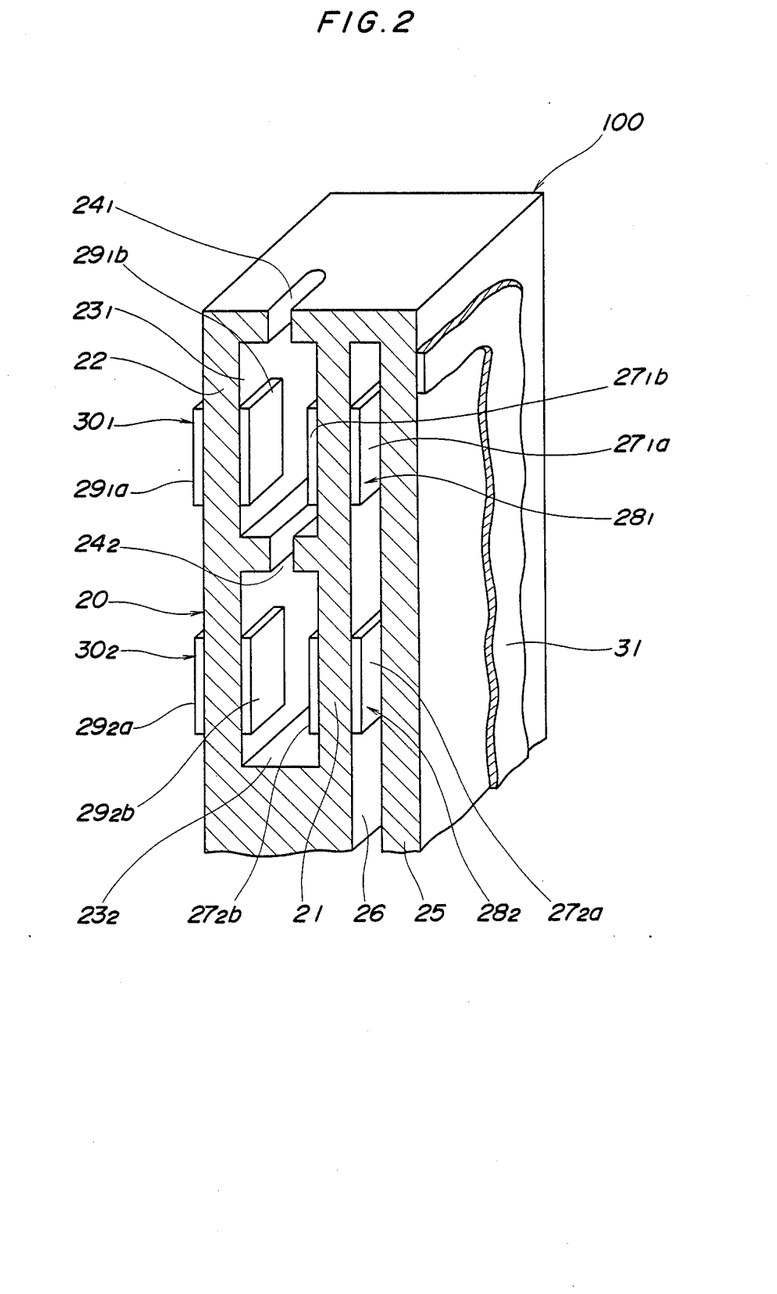
FIG. 2 is a perspective sectional view of the sensor in FIG. 1.

As shown in detail in FIG. 2, the sensor body 100 is in the form of a rectangular parallelepiped, and comprises a basic body 20 formed of a solid electrolytic material having oxygen ion-conductivity (e.g. zirconium dioxide ($ZrO_2$)).

The sensor body 100 shown in the figures is a type which has two oxygen concentration sensor elements longitudinally arranged, each having a cell element and an oxygen pumping element. The basic body 20 of the sensor body 100 has first and second walls 21, 22 extending parallel with each other, between which first and second gas diffusion chambers (diffusion restriction regions) $23_1$, $23_2$ serving as gas diffusion-limiting zones are defined.

The first gas diffusion chamber $23_1$ is communicated with an exhaust pipe, not shown, of the engine through a first slit $24_1$ which is disposed such that exhaust gases in the exhaust pipe can be guided into the first gas diffusion chamber $23_1$ through the slit $24_1$. The exhaust gases within the first gas diffusion chamber $23_1$ is introduced into the second gas diffusion chamber $23_2$ through a second slit $24_2$ communicating between the two chambers $23_1$ and $23_2$. An air reference chamber 26 to be supplied with air or reference gas is defined between the first wall 21 and an outer wall 25 disposed adjacent the first wall 21 and extending parallel therewith.

In order to detect oxygen concentration within the first gas diffusion chamber $23_1$, a couple of electrodes $27_1a$, $27_1b$ formed of platinum (Pt) are mounted on opposite side surfaces of the first wall 21, which cooperate with the first wall 21 to form a cell element (sensing cell) $28_1$ for the first oxygen concentration sensor element, while another couple of electrodes $29_1a$, $29_1b$ are similarly mounted on opposite side surfaces of the second wall 22, which cooperate with the second wall 22 to form an oxygen-pumping element (pumping cell) $30_1$ for the first oxygen concentration sensor element.

On the other hand, in order to detect oxygen concentration within the second gas diffusion chamber $23_2$, a cell element $28_2$ for the second oxygen concentration sensor element having a couple of electrodes $27_2a$, $27_2b$, and an oxygen-pumping element $30_2$ for the second oxygen concentration sensor element having a couple of electrodes $29_2a$, $29_2b$ are respectively mounted on the first and second walls 21, 22, similarly to the cell element $28_1$ and the oxygen-pumping element $30_1$.

A heater (heating element) 31 is provided on an outer side surface of the outer wall 25, for heating the cell elements $28_1$, $28_2$ and the oxygen-pumping elements $30_1$, $30_2$ to activate them.

As shown in FIG. 1, the electrodes $27_1b$ and $29_1b$ for the first oxygen concentration sensor element, which are located on the first gas diffusion chamber $23_1$ side, are connected with each other (in the embodiment of FIG. 1, they are connected by a suitable electrically conductive member 32), and are connected to an inverting input terminal of an operational amplifier 41 through a line 1.

On the other hand, the other electrode $27_1a$ of the cell element $28_1$ for the first oxygen concentration sensor element is connected to an inverting input terminal of a differential amplifier circuit $42_1$ for the first oxygen concentration sensor element. The differential amplifier circuit $42_1$ forms a voltage-applying circuit (voltage-applying means) together with a reference voltage source $43_1$ connected to an non-inverting input terminal thereof for applying to the oxygen-pumping element $30_1$ a voltage corresponding to the difference between a voltage (cell element voltage) developed between the electrodes $27_1a$ and $27_1b$ of the cell element $28_1$ (in the FIG. 1 embodiment, the sum of a voltage on the line 1 and the cell element voltage) and a reference voltage Vso from the reference voltage source $43_1$.

In the present embodiment, the reference voltage Vso of the reference voltage source $43_1$ is normally set to a value of the sum of the cell element voltage developed across the cell element $28_1$ when the actual air-fuel ratio of a mixture supplied to the engine is equal to a stoichiometric mixture ratio, e.g. 0.45 volts and a predetermined reference voltage, hereinafter referred to, applied to a non-inverting input terminal of the operational amplifier 41. However, the reference voltage Vso can be changed temporarily to a value, e.g., 3.05 V, higher by a predetermined value than the above normal value, when the output of the $O_2$ sensor has its value corrected for deterioration of the $O_2$ sensor 1.

The differential amplifier circuit $42_1$ has an output end thereof connected to the electrode $29_1a$ of the oxygen-pumping element $30_1$ remote from the first gas diffusion chamber $23_1$ by way of a switch $44_1$ of a switching circuit 44. The switching circuit 44 is controlled to close or open in dependence on activation and non-activation of the sensor body 100 as well as on operating conditions of the engine. More specifically, when the sensor body 100 is inactivated, both of the switches $44_1$ and $44_2$ are opened, and on the other hand, when it is activated, one of the switches is closed in response to operating conditions of the engine.

The non-inverting input terminal of the operational amplifier circuit 41 is connected to a reference voltage source 45 to be supplied with the predetermined reference voltage therefrom. A current-detecting resistance 46 for detecting pumping current Ip is connected between an output terminal of the operational amplifier circuit 41 and the line 1 or an inverting input terminal of the operational amplifier circuit 41. That is, the resistance 46 also serves as the negative feedback resistance of the operational amplifier circuit 41.

In the operational amplifier 41 connected as above, provided that there is no offset in the output of the circuit 41, when the actual air-fuel ratio is equal to the stoichiometric ratio, no pumping current Ip flows in the line 1 and is applied to the inverting input terminal of the circuit 41 according to the input level setting for the differential amplifier $42_1$, and then the output voltage is equal to the reference potential at the non-inverting input terminal and an electric potential at the inverting input terminal is also equal to the reference potential. On the other hand, when the actual air-fuel ratio is not equal to the stoichiometric ratio, pumping current is supplied to the inverting input terminal, an output voltage is generated at the output of the circuit 41, which corresponds to the amplification degree or factor (even if it is 1) determined by the value of the resistance 46. Although the output voltage varies in response to the magnitude of the pumping current Ip, the potential at the inverting input terminal is maintained at a constant value substantially equal to the reference potential at the non-inverting input terminal due to the action of the operational amplifier 41.

More specifically, in the above described construction, when no pumping current Ip flows in the line 1, i.e. Ip is zero, the output voltage $I_{PVW}$ of the operational amplifier 41 (i.e. the voltage at one end of the resistance 46) is made equal to the reference voltage $V_{REF}$ from the reference voltage source 45, and at the same time a voltage $V_{CENT}$ applied to the inverting input terminal (i.e. the voltage on the line 1 and at the other end of the resistance 46) is made equal to the reference voltage $V_{REF}$.

As described above, the voltage $V_{CENT}$ on the line 1 and accordingly at the other end of the resistance 46 is maintained substantially at the voltage $V_{REF}$, irrespective of whether the pumping current Ip assumes zero or varies. On the other hand, the voltage at the one end of the resistance 46 connected to the output of the operational amplifier circuit 41 is varied in response to the direction of the pumping current Ip (the positive direction or the negative direction) and the amount of the current Ip. Therefore, the voltage $V_{CENT}$ is a reference value (reference voltage) for detecting current flowing through the oxygen-pumping element and calculating the air-fuel ratio based on the detected current value.

In this sense, the potential on the line 1 is not the earth potential, but the whole system including the line 1 and the current-detecting resistance 46 is raised in potential from the ground level by the reference voltage $V_{REF}$. Consequently, when the pumping current Ip is determined from a potential difference between the opposite ends of the current-detecting resistance 46, that is, from the respective votages $V_{CENT}$ and $I_{PVW}$, as hereinafter described, the reference value $V_{CENT}$ as well as the other end voltage $I_{PVW}$ are always positive voltages, irrespective of whether the pumping current Ip flows in the positive direction or in the negative direction in response to the air-fuel ratio, thereby facilitating the calculation of the air-fuel ratio.

Further, the raising-up of the reference voltage of the pumping current detecting system to the constant reference voltage as above is advantageous for avoiding erroneous detection of the current due to noise, especially high level noise such as ignition pulse noise of the engine.

The voltage $V_{REF}$ of the reference voltage source 45 of the operational amplifier circuit 41 is set to a predetermined voltage (e.g. 2.5 volts) also for ensuring the above described advantage.

The second oxygen concentration sensor element of the sensor body 100 has a similar construction to the first oxygen concentration sensor element. That is, in the voltage-applying circuit and the switching circuit 44, there are respectively provided a differential amplifier circuit $42_2$, a reference voltage source $43_2$, and the aforementioned switch $44_2$. The switch $44_2$ is connected to the outer side electrode $29_2a$ of the oxygen-pumping element $30_2$, and the respective inner side electrodes $27_2b$ and $29_2b$ of the cell element $28_2$ and the oxygen-pumping element $30_2$ are both connected to the line 1, so that, during the use of the second oxygen concentration sensor element, the pumping current Ip flowing through the oxygen-pumping element $30_2$ flows in the line 1.

The output voltage $I_{PVW}$ of the operational amplifier circuit 41 and the voltage $V_{CENT}$ on the line 1, at the opposite ends of the current-detecting resistance 46, are supplied to an input port 401 of an electronic control unit (hereinafter called "the ECU") 4 as voltage-detecting means and are at the same time supplied to respective inputs of a differential amplifier circuit 47.

The differential amplifier circuit 47 amplifies the difference between the voltage $V_{CENT}$ and the output voltage $I_{PVW}$ of the operational amplifier circuit 41, and thus serves to improve the accuracy of a signal indicative of a voltage detected from pumping current Ip which assumes 0 or a value close thereto, i.e. where the actual air-fuel ratio is within a predetermined range about the stoichiometric air-fuel ratio of the mixture. In the differential amplifier circuit 47, the $I_{PVW}$ signal is amplified by a predetermined magnification $\alpha$, e.g. 5 times, to be produced as a voltage $I_{PVN}$.

The output voltage $I_{PVN}$ of the differential amplifier circuit 47 is obtained by the following equation, and is also supplied to the input port 401:

$$I_{PVN} = -5(I_{PVW} - V_{CENT}) + V_{CENT} \qquad \ldots (1)$$

Therefore, three voltage signals, i.e. $V_{CENT}$ as the reference voltage, $I_{PVW}$, and $I_{PVN}$ are supplied to the input port 401 for calculating the air-fuel ratio based on the pumping current Ip. Although the pumping current can be detected by using only the voltages $V_{CENT}$ and $I_{PVW}$ (a first manner of calculating the pumping current Ip), it can be more accurately detected by additionaly using the voltage $I_{PVN}$ (a second manner of calculating the pumping current Ip) when the actual air-fuel ratio is in the vicinity of the stoichiometric air-fuel ratio of the mixture in which the pumping current Ip assumes small values.

Figure 7:
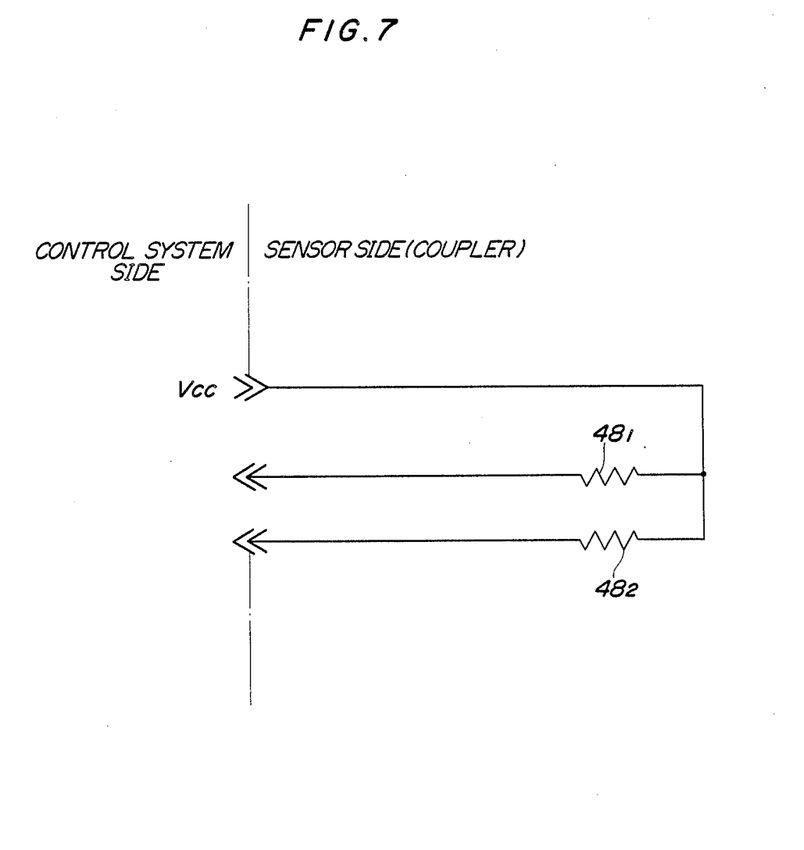
FIG. 7 is a diagram showing a wiring connection of label resistances.

Also supplied to the input port 401 is variation correcting value information for correcting variations in the detected actual air-fuel ratio due to variations between sensor bodies used. This information may be supplied individually for each of the first and second oxygen concentration sensor elements, if the sensor body 100 has two oxygen sensor elements as in the illustrated embodiment of the invention. Specifically, the information may be supplied by utilizing label correction resistances $48_1$ and $48_2$, as shown in FIG. 7.

The values of the label correction resistances $48_1$ and $48_2$ are set to values corresponding to variations in the characteristics of sensor bodies compared with a standard sensor body. The degree of variation in the characteristics of individual sensor body is indicated by a label indicative of its resistance value. The label correction resistances $48_1$ and $48_2$ are used together with the sensor body 100 used. That is, for instance, they may be provided within a connecting coupler, not shown, arranged in a wire harness, not shown, connecting the sensor body 100 to the ECU 4, hereinafter referred to. When the sensor body 100 is electrically connected to the ECU 4, respective one ends of the resistances $48_1$, $48_2$ are connected to a predetermined voltage source Vcc, as shown in FIG. 7, whereby the variation correcting value information corresponding to their resistance values is inputted through the other ends of the resistances.

The input port 401 of the ECU 4 is provided therein with an A/D (analog-to-digital) converter, which converts the above-mentioned input analog signals to digital signals.

The ECU 4 is supplied with respective output signals from a throttle valve opening ($\theta_{TH}$) sensor 10, and an intake pipe absolute pressure ($P_{BA}$) sensor 12 as engine parameter sensors, which then have their voltage levels shifted to a predetermined level by a level shifter circuit 402 and successively applied to the A/D converter 404 through a multiplexer 403. The A/D converter 404 of the input port 401 supplies the digitally-converted data to a central processing unit (hereinafter called "the CPU") 406 via a data bus 405.

An output signal from an engine speed (Ne) sensor 14 is applied to a waveform shaper circuit 407 to have its pulse waveform shaped, and the shaped signal is supplied to the CPU 406 as a top-dead center position (TDC) signal, as well as to a counter 408. The counter 408 counts the time interval between an immediately preceding pulse of the TDC signal and a present pulse of same, inputted thereto from the Ne sensor 14. The counted value Me is proportional to the reciprocal of the actual engine rotational speed Ne. The counter 408 supplies the counted value Me to the CPU 406 via the data bus 405.

Further connected to the CPU 406 via the data bus 405 are a read-only memory (hereinafter called "the ROM") 409, and a random access memory (hereinafter called "the RAM") 410, and driving circuits 412-414. The RAM 410 temporarily stores results of calculations executed within the CPU 406, while the ROM stores a control program to be executed within the CPU 406 for calculation of a fuel injection period $T_{OUT}$ of fuel injection valves 11, and other various programs, as well as various maps and tables.

The CPU 406 determines whether to energize or deenergize the heater 31 and whether to close or open the switches $44_1$ and $44_2$, and then supplies driving signals corresponding to the determinations to the heater 31 and the switching circuit 44 via the driving circuits 412 and 413.

The CPU 406 determines operating conditions of the engine such as a feedback control condition, based on the aforementioned various engine parameter signals including an output signal from the $O_2$ sensor 1, and calculates the fuel injection period of the fuel injection valves 11 in synchronism with TDC signal pulses in response to the determined engine operating conditions, based on a control program, not shown, by the use of the following equation (2):

$$T_{OUT} = T_i \times K_{O2} \times K_1 + K_2 \qquad \ldots (2)$$

where Ti represents a basic fuel injection period, in the ROM 409, in response e.g. to the absolute pressure $P_{BA}$ within the engine intake pipe, and the engine rotational speed Ne. $K_{O2}$ represents an air-fuel ratio correction coefficient, which is determined in response to oxygen concentration in the actual exhaust gases, based on a control program, not shown, when the engine is in the feedback control region, while it is set to a predetermined value when the engine is in an open loop control region. $K_1$ and $K_2$ respectively represent other correction coefficients and correction variables obtained in response to various engine parameter signals, and are set to such desired values as to optimize operating characteristics of the engine such as fuel consumption and accelerability.

The CPU 406 supplies the driving signals responsive to the results of the above calculation to the fuel injection valves 11 via the driving circuit 414. The air-fuel ratio is thus feedback-controlled to a desired ratio or stoichiometric ratio during the feedback operating condition of the engine.

The oxygen concentration is detected by the $O_2$ sensor in the following manner:

First, when the first oxygen concentration detecting element is selected by the switching circuit 44 as shown in FIG. 1, the exhaust gases are introduced into the first gas diffusion chamber $23_1$ through the first slit $24_1$ with operation of the engine. This causes a difference in oxygen concentration between the first gas diffusion chamber $23_1$ and the air reference chamber 26 into which air is introduced. Consequently, a voltage (sensor voltage) corresponding to the difference is developed between the electrodes $27_1a$ and $27_1b$ of the cell element $28_1$, which is added to the line 1 voltage $V_{CENT}$ and the same is applied to the inverting input terminal of the differential amplifier circuit $42_1$. As stated before, the reference voltage Vso supplied to the non-inverting input terminal of the differential amplifier circuit $42_1$ is set at the sum of a voltage developed across the cell element $28_1$ when the actual air-fuel ratio is equal to the stoichiometric air-fuel ratio, and the reference volta $V_{REF}$ supplied to the operational amplifier circuit 41.

Therefore, when the air-fuel ratio is on the lean side, the voltage between the electrodes $27_1a$ and $27_1b$ of the cell element $28_1$ lowers, while the line 1 voltage $V_{CENT}$ is maintained at $V_{REF}$, so that the sum of the voltage between the electrodes $27_1a$ and $27_1b$ and the $V_{CENT}$ becomes lower than the reference voltage Vso. Thus, the output level of the differential amplifier circuit $42_1$ becomes positive, and the positive level voltage is applied to the oxygen-pumping element $30_1$ via the switch $44_1$. By applying the positive level voltage, when the oxygen-pumping element $30_1$ is activated, oxygen present within the gas diffusion chamber $23_1$ is ionized, whereby the resulting ions move through the electrode $29_1b$, the second wall 22, and electrode $29_1a$ to be emitted therefrom as oxygen gas or pumped out of the $O_2$ sensor 1. Then, the pumping current Ip flows from the electrode $29_1a$ to the electrode $29_1b$ and flows through the current-detecting resistance 46 via the line 1. At this time, the pumping current Ip flows from the line 1 to the output side of the operational amplifier circuit 41.

On the other hand, when the air-fuel ratio is on the rich side, the sum of the voltage between the electrodes $27_1a$ and $27_1b$ of the cell element $28_1$ and the line 1 voltage $V_{CENT}$ becomes higher than the reference voltage Vso, so that the output level of the differential amplifier circuit $42_1$ becomes negative. Consequently, reversely to the above described action, external oxygen is pumped into the gas diffusion chamber $23_1$ through the oxygen-pumping element $30_1$, and simultaneously the pumping current Ip flows from the electrode $29_1$ to the electrode $29_1a$ and flows through the current-detecting resistance 46, that is, in the direction of flow of the pumping current Ip reverse to that in the above case.

When the actual air-fuel ratio is equal to the stoichiometric air-fuel ratio, the sum of the voltage between the electrodes $27_1a$ and $27_1b$ of the cell element 28 and the line 1 voltage $V_{CENT}$ becomes equal to the reference voltage Vso, so that the pumping-in and -out of oxygen is not effected, whereby no pumping current flows (that is, the pumping current Ip is zero).

As described above, since the pumping-in and -out of oxygen and hence the pumping current Ip are controlled so as to maintain the oxygen concentration in the gas diffusion chamber $23_1$ at a constant level, the pumping current Ip assumes a value proportional to the oxygen concentration of the exhaust gases on both the lean and rich sides of the actual air-fuel ratio.

Signals for detecting the amount of the pumping current Ip flowing through the current-detecting resistance 46, e.g. signals indicative of respective voltages $I_{PVW}$, $V_{CENT}$, $I_{PVN}$ at the opposite ends of the resistance 46 are supplied to the ECU 4.

Similarly to the first oxygen concentration sensor element, when the second oxygen concentration sensor element is used (that is, when the switch $44_2$ of the switching circuit 44 is closed, as reversely to the position shown in FIG. 1), the pumping-in and -out of oxygen is controlled so as to maintain the oxygen concentration in the second gas diffusion chamber $23_2$ at a constant value, that is, the voltage between the electrodes $27_2a$ and $27_2b$ of the cell element $28_2$ is feedback-controlled to be maintained at a constant value, and at the same time the signals indicative of the voltages $I_{PVW}$, $V_{CENT}$, $I_{PVN}$ for detecting the pumping current Ip flowing during the feedback control are supplied to the ECU 4 as outputs of the second oxygen concentration sensor element.

Figures 3, 3B:
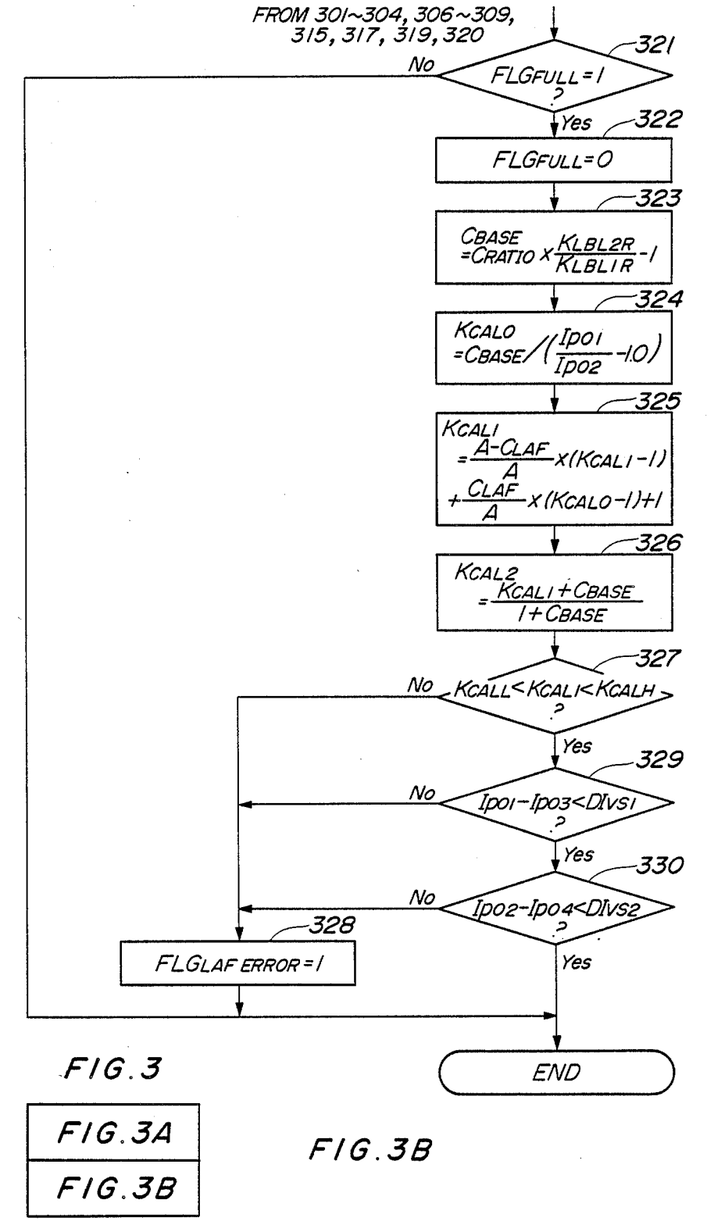
FIGS. 3, 3A and 3B are a flowchart of a subroutine for determining the deterioration of the sensor in FIG. 1.
Figure 3A:
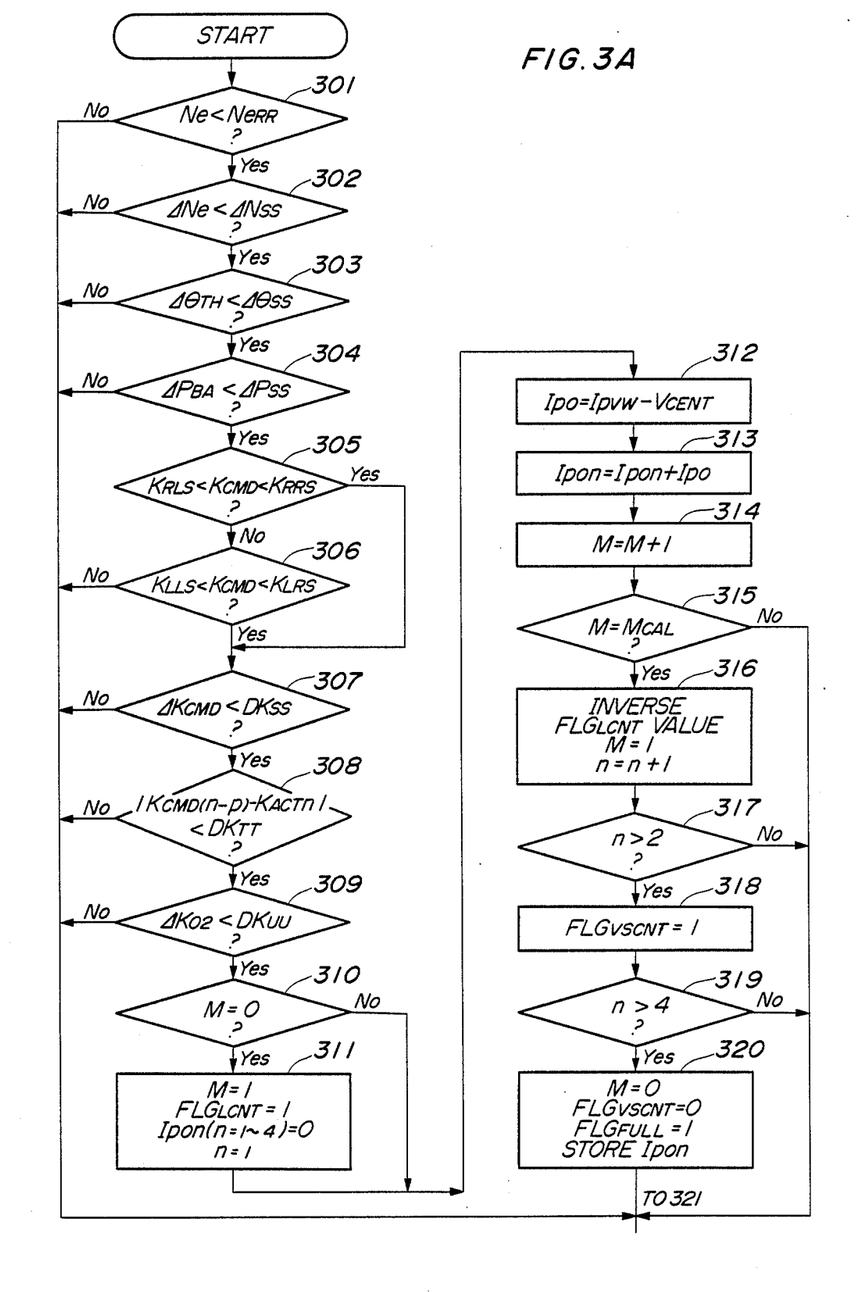

FIG. 3 shows a subroutine for determining the deterioration of the $O_2$ sensor 1, according to the method of the invention, which is executed upon generation of each pulse of the TDC signal and in synchronism therewith.

At steps 301 to 309, it is first determined whether or not conditions under which the deterioration of the O2 sensor 1 is to be determined, are fulfilled depending upon engine operating conditions and the controlled air-fuel ratio.

Specifically, first, it is determined at a step 301 whether or not the rotational speed Ne of the engine is lower than a predetermined value $Ne_{RR}$, e.g., 5,000 rpm, defining the lower limit of a predetermined high rotational speed region. If $Ne \geq Ne_{RR}$ is satisfied, that is, if the engine is in the predetermined high rotational speed region, it is determined that one of the deterioration-determining conditions is not satisfied, and the program proceeds to a step 321, hereinafter referred to.

If the answer to the question of the step 301 is affirmative or Yes, that is, if the engine is not in the predetermined high rotational speed region, it is determined at steps 302 to 304 whether or not the engine is in stable operation, by determining whether or not respective rates of change in the engine rotational speed $\Delta Ne$, the throttle valve opening $\Delta \theta_{TH}$, and the intake pipe absolute pressure $\Delta P_{BA}$ are smaller than respective predetermined values, $\Delta N_{SS}$, e.g., 10 rpm; $\Delta \theta_{SS}$, e.g., 0.5 degrees; and $\Delta P_{SS}$, e.g., 5 mmHg. Each of the rates of change $\Delta Ne$, $\Delta \theta_{TH}$, and $\Delta P_{BA}$ is the difference in parameter value between the present loop and the immediately preceding loop, i.e., the difference between a parameter value obtained upon generation of an immediately preceding TDC signal pulse and a present one. If at least one of the answers to the questions of the steps 302 to 304 is negative or No, that is, if at least one of $\Delta Ne \geq \Delta N_{SS}$, $\Delta \theta_{TH} \geq \Delta \theta_{SS}$, and $\Delta P_{BA} \geq \Delta P_{SS}$ is satisfied, it is considered that the engine is not in stable operation, which means that conditions for the deterioration determination are not fulfilled, and the program proceeds to the step 321. On the other hand, if all the answers are affirmative or Yes, that is, if $\Delta Ne < \Delta N_{SS}$, $\Delta \theta_{TH} < \Delta \theta_{SS}$, and $\Delta P_{BA} < \Delta P_{SS}$ are all satisfied, it is determined that the engine is in stable operation, and the program proceeds to steps 305 et seq.

At steps 305 and 306, it is determined whether or not a desired air-fuel ratio coefficient (hereinafter called "the desired ratio coefficient") $K_{CMD}$ corresponding to a desired air-fuel ratio is within a predetermined range. Specifically, it is first determined at the step 305 whether or not $K_{RLS} < K_{CMD} < K_{RRS}$ is satisfied, wherein $K_{RLS}$ and $K_{RRS}$ are first and second predetermined values on the rich side, e.g., 1.1 and 1.3, respectively, both larger than 1.0, and it is then determined at the step 306 whether or $K_{LLS} < K_{CMD} < K_{LRS}$ is satisfied, wherein $K_{LLS}$ and $K_{LRS}$ are first and second predetermined values on the lean side, e.g., 0.7 and 0.9, both smaller than 1.0.

The desired ratio coefficient $K_{CMD}$ is set in accordance with a subroutine, not shown, in response to engine operating conditions such that it is set to 1.0 when the desired air-fuel ratio is equal to the stoichiometric ratio, e.g., 14.7, and set to a value larger than 1.0 when the desired air-fuel ratio is richer than the stoichiometric ratio, and to a value smaller than 1.0 when the desired air-fuel ratio is leaner than the stoichiometric ratio.

If both the answers to the questions of the steps 305 and 306 are negative or No, that is, if $K_{RLS} < K_{CMD} < K_{RRS}$ and $K_{LLS} < K_{CMD} < K_{LRS}$ are not satisfied and the desired ratio coefficient $K_{CMD}$ is not within either of the predetermined ranges, it is judged that the actual air-fuel ratio is not stable, and the program proceeds to the step 321. On the other hand, if one of the answers is affirmative or Yes, that is, if the desired ratio coefficient $K_{CMD}$ is within one of the predetermined ranges on the rich and lean sides, the program proceeds to a step 307. Incidentally, a value of $K_{CMD}$ at and in the vicinity of 1.0, at which the desired air-fuel ratio is equal to the stoichiometric ratio, is not covered by either of the above predetermined ranges for prohibiting the deterioration determination at and in the vicinity of 1.0, because the pumping current Ip then assumes a value of nearly zero, making it difficult to effect the deterioration determination with accuracy.

At the step 307, it is determined whether or not a rate of change $\Delta K_{CMD}$ is smaller than a predetermined value $DK_{SS}$, e.g., 0.05. If the answer is negative or No, that is, if $\Delta K_{CMD} \geq DK_{SS}$ is satisfied, it is judged that the desired air-fuel is largely varying, and the program proceeds to the step 321.

Figure 4:
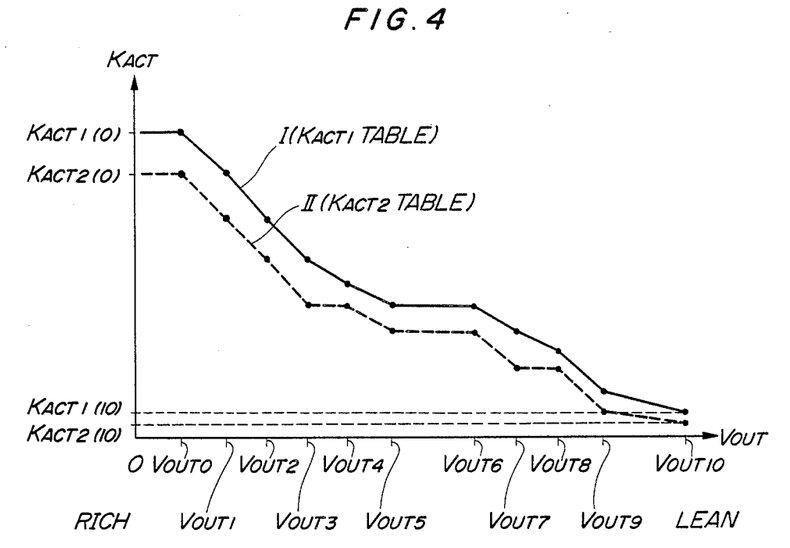
FIG. 4 is a graph showing a table of an actual air-fuel ratio-dependent coefficient $K_{ACT}$ applied in a step 308 of the subroutine of FIG. 3.

If the answer to the question of the step 307 is affirmative or Yes, that is, if $\Delta K_{CMD} < DK_{SS}$ is satisfied, it is determined at a step 308 whether or not the absolute value of the difference between a value $K_{CMD(n-p)}$ of the desired coefficient $K_{CMD}$ assumed in a loop before the present loop by a predetermined number P of loops and a value $K_{ACTn}$ of an actual ratio coefficient $K_{ACT}$, hereinbelow mentioned, assumed in the present loop, i.e., $|K_{CMD(n-p)} - K_{ACTn}|$ is smaller than a predetermined value $DK_{TT}$, e.g., 0.05. The actual ratio coefficient $K_{ACT}$ corresponds to the actual air-fuel ratio which has been detected by the O₂ sensor 1. As the value $K_{ACT}$, a value $K_{ACT1}$ for the first sensor element and a value $K_{ACT2}$ for the second sensor element are determined in response to a voltage value $V_{OUT}$ converted from the pumping current Ip in accordance with a table shown in FIG. 4. The value of $K_{ACT}$ is set such that it is set to 1.0 when the air-fuel ratio assumes the stoichiometric ratio, and set to a value larger than 1.0 when the air-fuel ratio is richer than the stoichiometric ratio, and a value smaller than 1.0 when the air-fuel ratio is leaner than same. In other words, the value of the actual ratio coefficient $K_{ACT}$ linearly varies at a nearly constant rate with change in the air-fuel ratio and hence the voltage-converted value $V_{OUT}$ on both the rich and lean sides.

If the answer to the question of the step 308 is negative or No, that is, if $|K_{CMD(n-p)} - K_{ACTn}| \geq DK_{TT}$ is satisfied, it is considered that the condition for the deterioration determination is not fulfilled, and the program proceeds to the step 321. Thus, when the difference between the desired air-fuel ratio and the actual air-fuel ratio is large, no deterioration determination is carried out so that it is possible to avoid inaccurate deterioration determination caused by change in the air-fuel ratio during deterioration determination, such as at the restart of the hot engine, as hereinbefore mentioned, and hence improve the accuracy of deterioration determination. Further, on such occasion, the feedback control is continued without being interrupted while the deterioration determination is inhibited so that the actual air-fuel ratio is promptly brought to the desired ratio, thereby improving the responsiveness of the air-fuel ratio control.

Figure 5:
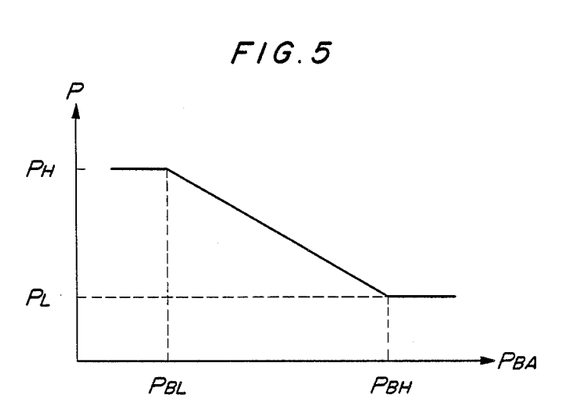
FIG. 5 is a graph showing a table of a predetermined number P of TDC signal pulses applied in the step 308 in FIG. 3.

Since as stated above the value of $K_{CMD}$ obtained in the loop before the present loop by the predetermined number P of loops is used in determining the difference between the desired air-fuel ratio and the actual air-fuel ratio at the step 308, time lag in the air-fuel ratio control system can be compensated for. FIG. 5 shows a table for setting a value of the predetermined number P. As shown in the figure, the value of the predetermined number P may be set depending upon the intake pipe absolute pressure $P_{BA}$. Specifically, it is set to a first predetermined value $P_H$, e.g., 20, when the value of $P_{BA}$ is equal to or lower than a first predetermined value $P_{BL}$ on the lower pressure side, and a second predetermined value $P_L$, e.g., 4, which is smaller than the first predetermined value $P_H$, when the value of $P_{BA}$ is equal to or higher than a second predetermined value $P_{BH}$ on the higher pressure side. When the value of $P_{BA}$ falls between the first and second predetermined values $P_{BL}$ and $P_{BH}$, the value of the predetermined number P is determined by an interpolation method. Since the present subroutine is executed upon generation of each pulse of the TDC signal and in synchronism therewith, the predetermined number P as the time lag can be determined from the engine rotational speed Ne and the intake pipe absolute pressure $P_{BA}$.

If the answer to the question of the step 308 is affirmative or Yes, that is, if $|K_{CMD(n-p)} - K_{ACTn}| < DK_{TT}$ is satisfied, it is determined at a step 309 whether or not a rate of change $\Delta KO_2$ in the air-fuel ratio correction coefficient $KO_2$ is smaller than a predetermined value $DK_{UU}$, e.g., 0.05. The air-fuel ratio correction coefficient $K_{O2}$, which is applied to the aforementioned equation (2) for actually correcting the air-fuel ratio, is determined based on the difference between the desired ratio coefficient $K_{CMD}$ and the actual ratio coefficient $K_{ACT}$ in accordance with a subroutine of FIG. 6, hereinafter described. If the answer to the question of the step 309 is negative or No, that is, if $\Delta K_{O2} \geq DK_{UU}$ is satisfied, it is judged that the actual air-fuel ratio is not stable, and the program proceeds to the step 321, whereas if the answer is affirmative or Yes, that is, if $\Delta K_{O2} < DK_{UU}$ is satisfied, it is judged that all the conditions for the deterioration determination are fulfilled according to the determination results so far obtained, and the program proceeds to steps 310 et seq.

At steps 310 to 320, addition of values of the pumping current Ip (hereinafter called merely "the addition") is executed for obtaining cumulated values Ipon used for carrying out the deterioration determination.

Specifically, at a step 310, it is first determined whether or not a control variable M is equal to 0. The control variable M is set to 0 upon initialization of the ECU 4 and at a step 320, hereinafter described, immediately after the addition has been done. If the answer to the question of the step 310 is affirmative or Yes, that is, if no addition has yet been carried out after initialization of the ECU 4, the program proceeds to a step 311, wherein the control variable M is set to 1 for selecting the first oxygen concentration sensor element to operate, followed by setting a flag $FLG_{LCNT}$ to 1 to indicate the selection of the first sensor element. Further, all the values of the cumulated value Ipon (n=1–4) of pumping current Ip are reset to 0, and a processing number n representing this resetting is set to 1. On this occasion, the respective reference voltages Vso of the reference voltage sources $43_1$, $43_2$ for the differential amplifiers $42_1$ and $42_2$ have been set to 2.95 V.

At a step 312, neutral or zero potential correction is effected. That is, the voltage $V_{CENT}$ is subtracted from the aforementioned output voltage $I_{PVW}$ of the operational amplifier circuit 41 to obtain a voltage value Ipo (hereinafter called "the pumping current value") corresponding to the pumping current Ip. Then, the obtained pumping current value Ipo is added to the cumulated value Ipon, which has been obtained so far before the present loop, to obtain a new cumulated value Ipon, at a step 313, and the control variable M is increased by 1, at a step 314. Then, it is determined at a step 315 whether or not the control variable M is equal to a predetermined value $M_{CAL}$, e.g., 20. If the answer is negative or No, the program proceeds to the step 321, wherein it is determined whether or not a flag $FLG_{FULL}$ has been set to 1. If the answer is negative or No, the program terminates. The flag $FLG_{FULL}$, which was set to 0 at the time of initialization of the ECU 4, is set to 1 at the step 320 immediately after all the additions of the cumulated values Ipo1–Ipo4 have been made. Consequently, the addition at the steps 312 to 314 is repeatedly carried out until the answer to the question of the step 315 becomes affirmative, i.e., until $M=M_{CAL}$ is satisfied, whereby a cumulated value Ipo1 corresponding to a value 1 of the processing number n, i.e., n=1, is obtained as the sum of values of the pumping current value Ipo added together a number $M_{CAL}$ of times.

If the answer to the question of the step 315 is affirmative or Yes, that is, if $M=M_{CAL}$ becomes satisfied, the program proceeds to a step 316, wherein the second oxygen concentration sensor element is selected to operate in place of the first oxygen concentration sensor element, and the flag $FLG_{LCNT}$ is inverted, i.e., it is set to 0 to indicate the selection of the second sensor element, the control variable M is reset to 1, and further the processing number n is increased by 1 into n=2.

Then, it is determined at a step 317 whether or not the processing number n is larger than 2. If the answer is negative or No, the program proceeds to the step 321. On this occasion, the processing number n is equal to 2 so that the answer to the question of the step 317 becomes negative or No, and further the answer to the question of the step 321 becomes negative or No. As a result, the addition at the steps 312 to 314 is further repeatedly carried out to obtain a second cumulated value Ipo2 corresponding to n=2 as the sum of values of the pumping current value Ipo added together the number $M_{CAL}$ of times, similarly to the above-mentioned cumulated value Ipo1.

If the answer to the question of the step 315 is again becomes affirmative or Yes, i.e., $M=M_{CAL}$ is satisfied, the step 316 is again executed and the first oxygen concentration sensor element is selected in place of the second oxygen concentration sensor element, followed by inversion of the flag $FLG_{LNCT}$ into 1, the control variable M is set to 1, and the processing number n is increased by 1 into n=3. On this occasion, the answer to the question of the step 317 is affirmative or Yes, that is, n>2 is satisfied, and then the program proceeds to a step 318.

At the step 318, the respective reference voltages Vso of the reference voltage sources $43_1$ and $43_2$, which have been set to 2.95 V, are changed to 3.05 V, followed by setting a value of a flag $FLG_{VSCNT}$, which has been set to 0 upon initialization of the ECU 4, to 1 to indicate the change of Vso. Then, it is determined at a step 319 whether or not the processing number n is larger than 4. If the answer is negative or No, the program proceeds to the step 321. As can be understood from the above description, a third cumulated value Ipo3 corresponding to n=3 and a fourth cumulated value Ipo4 corresponding to n=4 are, respectively, obtained as the sums of values of the pumping current value Ipo each added together the number $M_{CAL}$ of times.

Immediately after all the cumulative values Ipo1–Ipo4 have been obtained, the following execution of the step 316 renders the processing number n equal to 5, whereby the answer to the question of the step 319 becomes affirmative or Yes. That is, all the cumulated values Ipo1–Ipo4 of the pumping current value Ipo have been determined. Then, the program proceeds to a step 320, wherein the control variable M as well as the flag $FLG_{VSCNT}$ are both set to 0, and the flag $FLG_{FULL}$ is set to 1. The cumulated values Ipo1–Ipo4 obtained are stored into the RAM 410, and the program proceeds to the step 321. In the above described manner, the cumulated values Ipo1–Ipo4 of the pumping current Ipo are calculated and stored in relation to respective four combinations of the selected oxygen concentration sensor elements and the set values of the reference voltages Vso of the reference voltage sources $43_1$, $43_2$ of the differential amplifier $42_1$, $42_2$, as shown in the following table:

| CUMULATED VALUE Ipon | SENSOR ELEMENT | REFERENCE VOLTAGE Vso |
| --- | --- | --- |
| Ipo1 | First Sensor Element | 2.95 V |
| Ipo2 | Second Sensor Element | 2.95 V |
| Ipo3 | First Sensor Element | 3.05 V |
| Ipo4 | Second Sensor Element | 3.05 V |

In the step 321, it is determined whether or not the flag $FLG_{FULL}$ has been set to 1. On this occasion, the answer is affirmative or Yes, because of the execution of the step 320. Then the flag $FLG_{FULL}$ is reset to 0 at a step 322, and the program proceeds to steps 323 et seq. for carrying out the deterioration determination.

First, at the step 323, a basic value $C_{BASE}$ for carrying out the deterioration determination is calculated by the use of label-resistance correction coefficients $K_{LBL1R}$ and $K_{LBL2R}$, each of which has been determined from label-resistance value information from the label resistances $48_1$, $48_2$ on the side of the first and second oxygen concentration sensor elements, by the use of the following equation:

$$CBASE = C_{RATIO} \times K_{BL2R}/K_{BL1R} - 1.0 \quad \ldots (3)$$

where $C_{RATIO}$ represents a constant value, which has been set beforehand depending upon the difference in diffusion resistance between the first and second oxygen concentration sensor elements.

Then, a provisional value $K_{CAL0}$ of a first deterioration determination coefficient $K_{CAL1}$ for determining the deterioration of the first oxygen concentration sensor element is calculated at a step 324 by the use of the following equation:

$$K_{CAL0} = C_{BASE}/[(Ipo1/Ipo2) - 1.0] \quad \ldots (4)$$

where the provisional value $K_{CAL0}$, which represents a deviation of the output of the first sensor element from that of the second sensor element at the time of the present deterioration determination, and is set to 0 upon initialization of the ECU 4 and stored in a backup RAM together with the first deterioration determination coefficient $K_{CAL1}$ and a second deterioration determination coefficient $K_{CAL2}$, hereinafter described.

Then, the first deterioration determination coefficient $K_{CAL1}$ is calculated by the use of the following equation:

$$K_{CAL1} = (A - C_{LAF})/A \times (K_{CAL}' - 1) + C_{LAF}(K_{CAL0} - 1)/A + 1 \quad \ldots (5)$$

where A represents a constant value, CLAF an averaging constant experimentally obtained, which is set to an appropriate value between 1 and A, and $K_{CAL1}'$ an average value of values of $K_{CAL1}$ obtained through past operation of the engine and stored.

Since the ratio of $K_{CAL0}$ to $K_{CAL1}'$ varies with the value of the averaging constant $C_{LAF}$, the deterioration determination can optimally be carried out by setting the averaging constant $C_{LAF}$ to such a value that best suits the type of an $O_2$ sensor, an air-fuel ratio feedback control system, etc. to be applied.

Then, the second deterioration determination coefficient $K_{CAL2}$ for determining the deterioration of the second oxygen concentration sensor element is calculated at a step 326, by the use of the following equation:

$$K_{CAL2} = (K_{CAL1} + C_{BASE})/(1 + C_{BASE}) \quad \ldots (6)$$

Then, it is determined at a step 327 whether or not the first deterioration determination coefficient $K_{CAL1}$ is larger than a lower-limit value $K_{CALL}$, e.g., 0.4, and smaller than an upper-limit value $K_{CALH}$, e.g., 1.6. The first deterioration determination coefficient $K_{CAL1}$ should assume a normal value of 1.0 when there is no deterioration in the $O_2$ sensor 1. Therefore, if the answer to the question of the step 327 is negative or No, that is, if $K_{CAL1} \leq K_{CALL}$ or $K_{CAL1} \geq K_{CALH}$ is satisfied, it is judged that there is heavy deterioration in the $O_2$ sensor 1, and the program proceeds to a step 328, wherein the flag $FLG_{LAFERROR}$ is set to 1 to indicate the above deteriorated state of the $O_2$ sensor 1, thereby giving warning to the driver by lightening an alarm light, for example.

If the answer to the question of the step 327 is affirmative or Yes, that is, if $K_{CALL} < K_{CAL1} < K_{CALH}$ is satisfied, it is determined at a step 329 whether or not the difference between the first cumulated value Ipo1 and the third cumulated value Ipo3 of the pumping current value Ipo is smaller than a first predetermined value $DI_{VS1}$, and at a step 330 whether or not the difference between the second cumulated value Ipo2 and the fourth cumulated value Ipo4 of the pumping current value Ipo is smaller than a second predetermined value $DI_{VS2}$. These determinations are carried out based on the output characteristic of this type of sensor as shown in FIG. 8 for judging the degree of deterioration in the first and second oxygen concentration sensor elements of the $O_2$ sensor 1 by determining the degree of deviation in the pumping current value Ipo obtained by the changeover of the reference voltage Vso value of the differential amplifier $42_1$, $42_2$, or voltage applied to the sensor, from 2.95 V to 3.05 V or vice versa. As previously stated with reference to FIG. 8, a sensor of this kind generally has such a characteristic that the pumping current value Ipo hardly varies even with variation in the voltage applied to the sensor within a predetermined range corresponding to the flat curve portion A. Therefore, it is possible to judge the degree of deterioration in the $O_2$ sensor 1 by executing the steps 329 and 330. Therefore, if either one of the answers to the questions of the steps 329 and 330 is negative or No, that is, if $Ipo1 - Ipo3 \leq DI_{VS1}$ or $I_{PO2} - I_{PO4} \geq DI_{VS2}$ is satisfied, it is judged that there is heavy deterioration in the $O_2$ sensor 1 and the aforementioned step 328 is executed, followed by terminating the program.

In this embodiment, only the first deterioration determination coefficient $K_{CAL1}$ is used at the step 327 for determining the deterioration of the $O_2$ sensor 1. However, the second deterioration determination coefficient $K_{CAL2}$ may also be used in a similar manner for determining the deterioration of the $O_2$ sensor 1. Further, these coefficients $K_{CAL1}$ and $K_{CAL2}$ are used in a subroutine, not shown, as described in detail in U.S. Ser. No. 07/338,987 filed by the assignee of the present application, for correcting the output of the $O_2$ sensor.

As described above, the method of the invention utilizes the arrangement of the $O_2$ sensor that the oxygen-pumping elements $30_1$, $30_2$ are provided separately from the respective corresponding cell elements $28_1$, $28_2$ of the first and second oxygen concentration sensor elements such that the pumping current Ip does not flow through the cell elements $28_1$, $28_2$. Therefore, the pumping current Ip is free from a voltage drop across the cell elements $28_1$, $28_2$ due to the internal resistance of same, to thereby enable accurate determination of deterioration of the $O_2$ sensor based on the relationship between the accurately detected applied voltage and the pumping current $I_{po}$.

Figure 6:
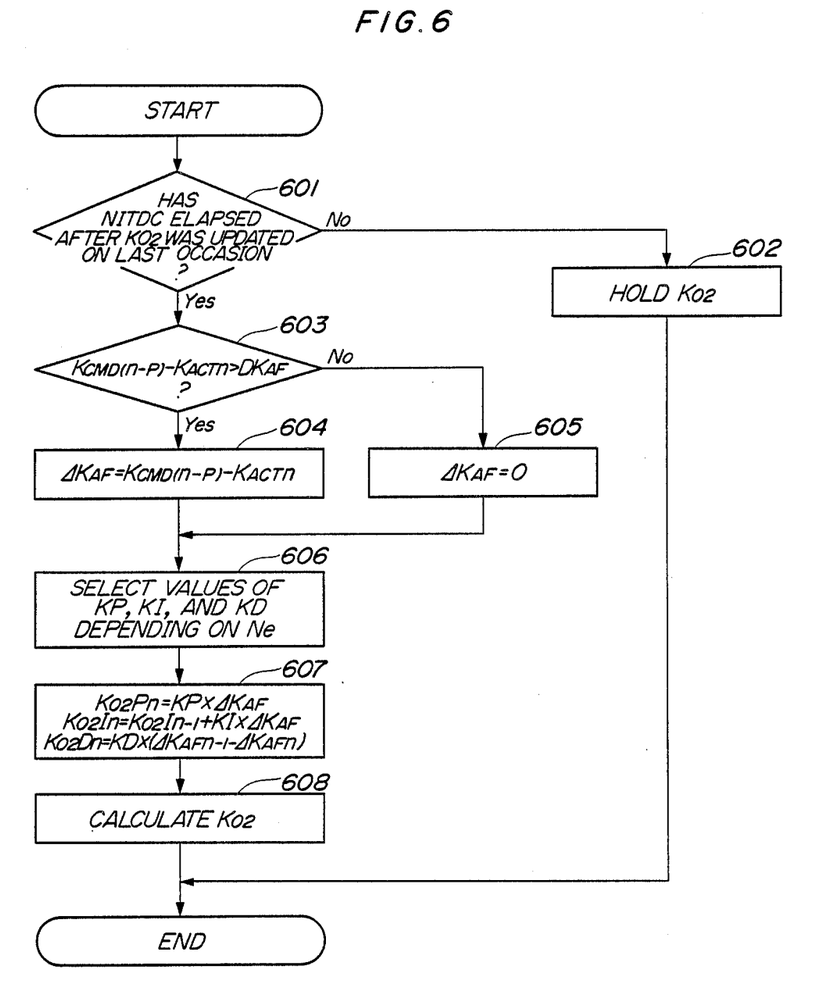
FIG. 6 is a flowchart of a subroutine for calculating an air-fuel ratio correction coefficient $K_{O2}$.

FIG. 6 shows a subroutine for calculating a value of the air-fuel ratio correction coefficient $K_{O2}$ applied to the step 309 in the subroutine of FIG. 3, which is executed upon generation of each pulse of the TDC signal and in synchronism therewith.

In the subroutine, it is first determined at a step 601 whether or not a pulse of the TDC signal has been generated a predetermined number NITDC of times, e.g., 4 times, after the air-fuel ratio correction coefficient $K_{O2}$ was updated on the last occasion. If the answer is negative or No, a value of $K_{O2}$ is held at a value obtained immediately before open-loop control on the last occasion, at a step 602, followed by terminating the program. Thus, the value of the $K_{O2}$ is updated whenever the predetermined number NITDC of TDC signal pulses have been generated.

If the answer to the question of the step 601 is affirmative or Yes, it is determined at a step 603 whether or not the difference between the value $K_{CMD(n-p)}$ of the desired ratio coefficient $K_{CMD}$, which has been obtained in a loop preceding the present loop by the predetermined number P of loops, and the value $K_{ACTn}$ of the actual coefficient $K_{ACT}$ in the present loop, i.e., $K_{CMD(n-p)} - K_{ACTn}$, is larger than a predetermined value $DK_{AF}$, similarly to the step 308 of FIG. 3. If the answer is affirmative or Yes, that is, if $K_{CMD(n-p)} - K_{ACTn} > DK_{AF}$ is satisfied, the value of the difference is applied as a difference $\Delta K_{AF}$ between the desired coefficient and the actual coefficient $K_{ACT}$, whereas if the answer is negative or No, that is, if $K_{CMD(n-p)} - K_{ACTn} \leq DK_{AF}$ is satisfied, it is considered that the difference between the desired air-fuel ratio and the actual air-fuel ratio is small so that the difference $\Delta K_{AF}$ is set to 0 at a step 605 for stabilizing the feedback control, and the program proceeds to a step 606.

At the step 606, respective values of a coefficient KP for proportional-control term, a coefficient KI for integral-control term, and a coefficient KD for differential-control term are selected from tables, not shown, stored in the RAM, depending on the engine rotational speed Ne. Then, the selected values of the coefficients KP, KI, and KD as well as the difference $\Delta K_{AF}$ calculated at the step 604 or 605 are applied to the following equations for calculating values of the proportional-control term $K_{O2Pn}$, integral-control term $K_{O2In}$, and differential-control term $K_{O2Dn}$, at a step 607.

$$K_{O2Pn} = KP \times \Delta K_{AF} \qquad \ldots (7)$$

$$K_{O2In} = K_{O2In-1} + KI \times \Delta K_{AF} \qquad \ldots (8)$$

$$K_{O2Dn} = KD \times (\Delta K_{AFn-1} - \Delta K_{AFn}) \qquad \ldots (9)$$

Then, the value of the air-fuel ratio correction coefficient $K_{O2}$ is calculated by summing up the calculated values of the proportional-control term $K_{O2Pn}$, the integral-control term $K_{O2In}$, and the differential-control term $K_{O2Dn}$, followed by terminating the program.

Although the above-described embodiment is applied to an $O_2$ sensor having two or first and second oxygen concentration sensor elements, this is not limitative, but the method according to the invention may be applied to an $O_2$ sensor having a single oxygen concentration sensor element, i.e. only one set of a cell element and an oxygen-pumping element.

What is claimed is:

1. A method of determining the deterioration of an oxygen concentration sensor for an internal combustion engine, said oxygen concentration sensor including:

at least one oxygen concentration sensor element, said oxygen concentration sensor element having an oxygen-pumping element and a cell element, said oxygen-pumping element and said cell element each being composed of a member of a solid electrolytic material having oxygen ion-conductivity, and a pair of electrodes having said member interposed therebetween, said oxygen-pumping element and said cell element defining a diffusion restriction region therebetween;

a current-detecting resistance serially connected to said oxygen-pumping element to form a series circuit therewith;

voltage-applying means for applying to said series circuit a voltage having a magnitude corresponding to a difference between a voltage produced between said electrodes of said cell element and a predetermined reference voltage; and current-detecting means for detecting pumping current from a voltage developed across said current-detecting resistance;

the method comprising the steps of:

(1) changing said predetermined reference voltage from a first predetermined value to a second predetermined value;

(2) detecting a difference between a value of said pumping current detected when said predetermined reference voltage assumes said first predetermined value and a value of said pumping current detected when said predetermined reference voltage assumes said second predetermined value;

(3) comparing said difference detected in said step (2) with a predetermined reference value; and (4) determining that there is deterioration in said oxygen concentration sensor when said difference is equal to or greater than said predetermined reference value.

2. A method as claimed in claim 1, wherein said oxygen concentration sensor includes first and second oxygen concentration sensor elements, and said steps (2)–(4) comprise:

(2a) detecting a first difference between a value of said pumping current detected by the use of said first oxygen concentration sensor element when said predetermined reference voltage assumes said first predetermined value and a value of said pumping current detected by the use of said first oxygen concentraion sensor element when said predetermined reference voltage assumes said second predetermined value;

(2b) detecting a second difference between a value of said pumping current detected by the use of said second oxygen concentration sensor element when said predetermined reference voltage assumes said first predetermined value and a value of said pumping current detected by the use of said second oxygen concentration sensor element when said predetermined reference voltage assumes said second predetermined value;

(3a) comparing said first difference with a first predetermined reference value;

(3b) comparing said second diffrence with a second predetermined reference value; and (4') determining that there is deterioration in said oxygen concentration sensor either when said first difference is equal to or greater than said first predetermined reference value or when said second difference is equal to or greater than said second predetermined reference value.

3. A method as claimed in claim 1, wherein said step (2) comprises detecting a difference between a cumulated value of values of said pumping current detected a predetermined number of times when said predetermined reference voltage assumes said first predetermined value and a cumulated value of values of said pumping current detected said predetermined number of times when said predetermined reference voltage assumes said second predetermined value.

4. A method as claimed in claim 2, wherein said steps (2a) and (2b) comprise:

(2a') detecting a first difference between a cumulated value of values of said pumping current detected by the use of said first oxygen concentration sensor element a predetermined number of times when said predetermined reference voltage assumes said first predetermined value and a cumulated value of values of said pumping current detected by the use of said first oxygen concentration sensor element said predetermined number of times when said predetermined reference voltage assumes said second predetermined value; and (2b') detecting a second difference between a cumulated value of values of said pumping current detected by the use of said second oxygen concentration sensor element a predetermined number of times when said predetermined reference voltage assumes said first predetermined value and a cumulated value of values of said pumping current detected by the use of said second oxygen concentration sensor element said predetermined number of times when said predetermined reference voltage assumes said second predetermined value.

5. A method as claimed in claim 1 wherein said determination of deterioration of said oxygen concentration sensor is carried out when said engine is in a predetermined stable operating condition.

6. A method as claimed in claim 5, wherein said predetermined stable operating condition is a condition where the rotational speed of said engine is lower than a predetermined value.

7. A method as claimed in claim 5, wherein said predetermined stable operating condition is a condition where a rate of change in the rotational speed of said engine is lower than a predetermined value.

8. A method as claimed in claim 5, wherein said predetermined stable operating condition is a condition where a rate of change in the opening of a throttle valve of said engine is lower than a predetermined value.

9. A method as claimed in claim 5, wherein said predetermined stable operating condition is a condition where a rate of change in absolute pressure within an intake pipe of said engine is lower than a predetermined value.

10. A method as claimed in claim 5, wherein said predetermined stable operating condition is a condition where a coefficient corresponding to a desired air-fuel ratio obtained in the present loop falls within a predetermined range about a stoichiometric ratio.

11. A method as claimed in claim 5, wherein said predetermined stable operating condition is a condition where a rate of change in said desired air-fuel ratio is lower than a predetermined value.

12. A method as claimed in claim 5, wherein said predetermined stable operating condition is a condition where a rate of change in a coefficient for correcting said actual air-fuel ratio is lower than a predetermined value.

13. A method as claimed in claim 1, further including the steps of:

(5) determining whether or not a difference between a desired air-fuel ratio and an actual air-fuel ratio represented by an output of said at least one oxygen concentration sensor element is smaller than a predetermined value, and (6) carrying out said determination of deterioration of said oxygen concentration sensor when it is determined that said difference obtained in said step (5) is smaller than said predetermined value.

14. A method as claimed in claim 13, wherein said step (5) comprises determining a first coefficient corresponding to said actual air-fuel ratio in the present loop from said output of said at least one oxygen concenteration sensor element, determining a second coefficient corresponding to said desired air-fuel ratio in a loop before the present loop by a predetermined number of loops, and determining whether or not a difference between the value of said first coefficient and the value of said second coefficient thus determined is smaller than a predetermined value.

* * * * *